US006443307B1

United States Patent
Burridge (10) Patent No.: US 6,443,307 B1
(45) Date of Patent: Sep. 3, 2002

(54) MEDICATION DISPENSER WITH AN INTERNAL EJECTOR

(76) Inventor: Michael D. Burridge, 975 Lilac Dr., Santa Barbara, CA (US) 93108

( * ) Notice: Subject to any disclaimer, the term of this patent is extended or adjusted under 35 U.S.C. 154(b) by 0 days.

(21) Appl. No.: 09/491,496

(22) Filed: Jan. 25, 2000

(51) Int. Cl.$^7$ ................................................. B65D 83/02
(52) U.S. Cl. ......................... 206/532; 206/469; 222/80
(58) Field of Search ............................. 222/80, 81, 83; 206/461, 469, 531, 532

(56) References Cited

U.S. PATENT DOCUMENTS

| 1,774,258 A | | 8/1930 | English | |
|---|---|---|---|---|
| 2,893,392 A | * | 7/1959 | Wagner et al. | |
| 2,974,787 A | | 3/1961 | Cooper | 206/63.2 |
| 4,015,717 A | | 4/1977 | Richardson et al. | 206/534 |
| 4,096,945 A | | 6/1978 | Melton, Jr. et al. | 206/469 |
| 4,103,772 A | | 8/1978 | Wiegner | 206/222 |
| 4,778,054 A | | 10/1988 | Newell et al. | 206/531 |
| 4,802,493 A | * | 2/1989 | Maganias | 128/743 |
| 5,054,499 A | * | 10/1991 | Swierczek | 128/770 |
| 5,071,034 A | | 12/1991 | Corbiere | 222/80 |
| 5,115,913 A | * | 5/1992 | Anhauser et al. | 206/440 |
| 5,255,812 A | | 10/1993 | Hsu | 220/277 |
| 5,348,158 A | | 9/1994 | Honan et al. | 206/531 |
| 5,396,986 A | | 3/1995 | Fountain et al. | 206/219 |
| 5,431,283 A | | 7/1995 | Weinstein et al. | 206/531 |
| 5,564,570 A | | 10/1996 | Jaszai | 206/523 |
| 5,816,404 A | | 10/1998 | Seidler | 206/461 |

* cited by examiner

Primary Examiner—David T. Fidei
(74) Attorney, Agent, or Firm—Lyon & Harr, LLP; Mark A. Watson (57) ABSTRACT

The present invention is embodied in an apparatus, such as a blister pack, having the capability to safely store and protect items such as medication in solid, soft or semi-solid, powder, or liquid form, while allowing such items to be easily and rapidly dispensed by a user. The dispenser of the present invention has a flexible upper membrane forming a dome. A lower membrane serves to seal items between the dispensers' upper and lower membranes. An annular-shaped internal cutter resides within the dome between the upper and lower membranes, oriented perpendicular to the membranes. Items are sealed within the chamber created by the structure of the cutter and the upper and lower membranes. The lower membrane is of sufficient strength to prevent inadvertent tearing or rupturing of the membrane, even when carried in a relatively hostile environment, such as with metal keys in a users pocket. However, the internal cutter is capable of cutting through this membrane by simply depressing the dome thereby providing an open path for rapid and complete evacuation of the chamber contents.

11 Claims, 6 Drawing Sheets

MEDICATION DISPENSER WITH AN INTERNAL EJECTOR

BACKGROUND OF THE INVENTION

1. Technical Field

This invention relates to an apparatus for protecting and dispensing items such as medication in solid, powder or liquid form, and more particularly, to an apparatus which can be used by a person to safely carry such items while protecting the items from damage or exposure and allowing the person to immediately and easily access those items.

2. Related Art

"Blister packs" or "soft packs" are sometimes used to carry items, such as specific dosage medication in pill or powder form, in readily accessible, individually sealed and sterile compartments. Individual compartments making up the blister pack may be opened exclusively of any other compartments in the pack. Typically, these compartments are opened by pushing the contents of the compartment through a frangible membrane sealing the compartment, or by peeling back a covering forming part of the compartment.

The frangible membrane used to seal the individual compartments of blister packs must be made weak enough that the contents of the compartment may be forced through the frangible wall or membrane without being damaged. However, the unfortunate result of this construction is that weak membranes are subject to tearing or rupturing. For example, if a blister pack is carried in a user's pocket along with a set of keys or other hard items, it is not uncommon for damage to the membranes sealing one or more compartments to occur. Damage to a compartment typically exposes the contents of that compartment to environmental conditions such as moisture or contamination that can render the contents unusable.

The frangible membrane used to seal a compartment may be made strong enough to minimize the possibility of inadvertent tearing or rupturing. However, while increased strength may appear desirable, the usefulness of such a configuration is limited in that forcing the contents of the compartment through the membrane can become increasingly difficult as the strength of the membrane is increased. Further, the structural integrity of the contents of the compartment must be considered when increasing the strength of the membrane. For example, nitroglycerin pills, often carried by a person suffering from angina pectoris, are very soft, having a consistency similar to compacted powdered sugar. Attempting to force such pills through even a very weak membrane will tend to pulverize the pills, with the result that the medication is difficult or impossible to ingest.

Further, it is often desirable to place liquids or powders within a compartment of a blister pack. It is difficult to force such compositions through a frangible membrane. Making a membrane weak enough to allow its use with liquids or powders creates a configuration that is extremely susceptible to damage by tearing and/or rupturing.

Blister pack configurations having coverings that may be peeled back to expose the contents of a compartment in the pack also have problems. For example, it is not uncommon for an area of the covering to tear away in such a manner as to expose more than one compartment. Where it is not desired to open or expose more than one compartment at a time, the contents of any additional fully or partially opened compartments may be exposed to moisture or other contaminants that render those contents unusable.

Further, a common problem associated with peelable coverings is that such coverings tend to give way suddenly as the surface area to which they are attached decreases while they are being peeled back. In such cases, the contents of the compartment enclosed by the cover may be flung out of the compartment as the cover suddenly gives way. This may result in damage or contamination of the contents, thereby rendering the contents unusable. In addition, such configurations are not suitable for use in containing liquids or powders, as the possibility of spillage is dramatically increased.

Various solutions have been devised in an attempt to address some of the problems described above. For example, some blister packs have sharp external prongs designed to pierce a cover or seal, then to pierce the skin against which such blister packs are pressed. These blister packs have been designed to deliver intracutaneous injections of liquid medication that coats the prongs. Such configurations are not capable of delivering powdered or solid medications or other items.

Other designs use cumbersome or complicated external cutter devices designed to cut the covering of a compartment in a blister pack. For example, some blister packs have external cutters that must be pressed through a frangible covering, rotated to cut or tear the covering, then pulled back or removed to expose the contents of the compartment. Such devices can be complicated and expensive to manufacture. Further, such devices may be difficult to operate, especially where they are designed to provide "child resistance," and/or where the user has trembling or unsteady hands, or is otherwise impaired.

Still other blister pack designs use sharpened prongs within the compartments of the pack to pierce a frangible covering to allow mixing of a binary compound contained within sub-compartments. However, simply piercing the covering in one or more places does not provide an adequate opening to allow the contents of a compartment to be quickly and completely evacuated or removed from the compartment. Often, especially with powders and liquids, a portion of the contents remains in the compartment and is lost because the prongs do not create a sufficient path for complete egress of the contents. Consequently, use of such designs requires either increasing the volume of the liquid or powder to account for the loss, or simply ignoring the issue altogether.

Still other solutions, such as requiring the blister pack to be placed within separate mechanisms having cutters designed to open one or more compartments, have been suggested. Such devices tend to be relatively expensive and complicated, especially where they must also function as a medication dispenser for liquid and/or powder medications.

Accordingly, there is a need for a blister pack that overcomes the problems associated with current blister pack designs. This blister pack would be sealed with a membrane or covering of sufficient strength to prevent inadvertent tearing or rupturing. To ensure that the contents of a compartment are protected during removal, the blister pack would not require that the contents of the compartment be forced through the membrane or covering in order to open the compartment, or that the covering be manually peeled back to expose the contents of the compartment. Further, the blister pack would work equally well with solids, powders, soft or semi-solid items, or liquids without requiring external cutters or opening devices. In addition, the blister pack would provide an open path for complete evacuation of liquids and powders. The blister pack would be extremely easy to operate, even where the user was in an impaired state, or had unsteady or shaking hands. Finally, the blister pack would be simple and inexpensive to manufacture.

SUMMARY OF THE INVENTION

To overcome the limitations in the related art described above, and to overcome other limitations that will become apparent upon reading and understanding the present application, the present invention is embodied in an apparatus, such as a blister pack, having the capability to safely store and protect items such as medication in solid, soft or semi-solid, powder, or liquid form, while allowing such items to be easily and rapidly dispensed by a user.

In general, the present invention is preferably embodied in a "pill pack" or "blister pack" having a flexible plastic upper membrane including at least one depressing dome. A lower membrane serves to seal items such as pills, powders, or liquids between the pill pack's upper and lower membranes. An annular-shaped internal punch or cutter resides within the depressing dome between the upper and lower membranes, oriented perpendicular to the membranes. Pills, powders, liquids or other items are sealed within the void or chamber created by the structure of the annular punch or cutter and the upper and lower membranes of the pill pack. One or more such chambers may be arranged in rows and/or columns to provide the desired amount of storage.

The lower membrane is of sufficient strength to prevent inadvertent tearing or rupturing of the membrane, even when carried in a relatively hostile environment, such as with metal keys in a users pocket. However, the internal cutter is capable of cutting through this membrane by simply depressing the dome thereby providing an open path for rapid and complete evacuation of the chamber contents.

In operation, a user preferably depresses the depressing dome which forces the annular cutter through the lower membrane, thereby opening the lower membrane and allowing the release of the contents of the chamber to the user. Unlike more complicated devices which require manipulation of external cutter devices, or carefully peeling back a membrane, a user having unsteady or shaking hands would be able to depress the dome to open the chamber thereby releasing the contents.

Further, because the volume of the chamber decreases as the dome is depressed, the internal pressure within the chamber is preferably increased prior to cutting the lower membrane. The increased pressure preferably serves to propel the contents out of the chamber as the lower membrane is cut. This feature is especially useful in dispensing powders and liquids.

For example, in one embodiment, the pill pack may be used with a medication carrier/inhaler for powdered medication. As the dome is depressed, the cutter cuts the lower membrane, and the increased pressure within the chamber propels the powder within the chamber into the inhaler where a user immediately inhales the powdered medication.

In addition, because there are no moving parts, simply an upper membrane having a flexible plastic dome with an internal cutter, the upper membrane may be inexpensively and easily fabricated by methods such as injection molding using a thermoplastic compound. The lower membrane may also be inexpensively and easily fabricated from any suitable material such as, for example, metal foil or plastic. The upper and lower membranes are preferably bonded together, using conventional techniques, to hermetically seal the contents of at least one chamber.

The foregoing and still further features and advantages of the present invention as well as a more complete understanding thereof will be made apparent from a study of the following detailed description of the invention in connection with the accompanying drawings and appended claims.

BRIEF DESCRIPTION OF THE DRAWINGS

Referring now to the drawings in which like reference numbers represent corresponding parts throughout.

FIG. 3 is a schematic side elevation of the dispenser of FIG. 1a;

FIG. 4 is a cut-away top view of the dispenser of FIG. 1a;

DETAILED DESCRIPTION OF THE INVENTION

In the following description of the invention, reference is made to the accompanying drawings, which form a part hereof, and in which is shown by way of illustration a specific example in which the invention may be practiced. It is to be understood that other embodiments may be utilized and structural changes may be made without departing from the scope of the present invention.

Overview

The present invention is embodied in a dispensing apparatus, such as a blister pack, having the capability to safely store and protect items such as medication in solid, soft or semi-solid, powder, or liquid form, while allowing such items to be easily and rapidly dispensed by a user by simply depressing a flexible depressing dome.

A dispenser according to the present invention is preferably fabricated of a thermoplastic compound, but may be fabricated of any suitably flexible material that will not react chemically with the contents stored within the dispenser. Further, because the material of the dispenser is preferably non-permeable to air and/or moisture, the dispenser provides a hermetically sealed storage environment.

Figure 1A:
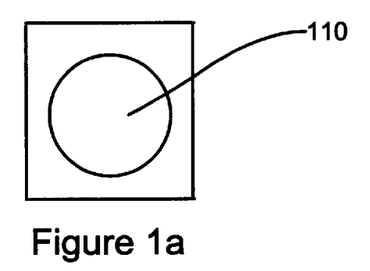
FIG. 1a is a top view of a dispenser according to the present invention.
Figure 1B:
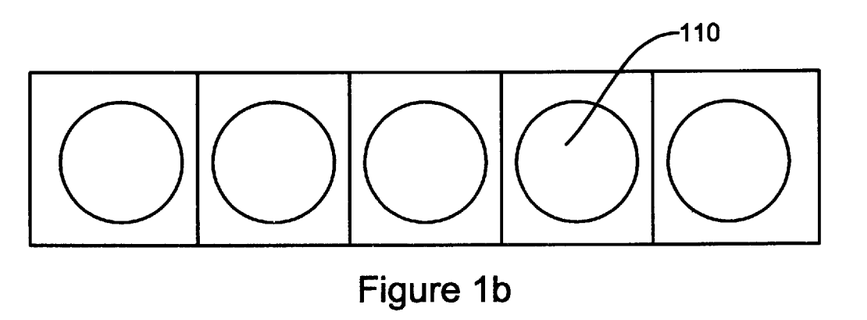
FIG. 1b is a top view of the dispenser of FIG. 1a showing dispensing chambers arranged in a row.
Figure 1C:
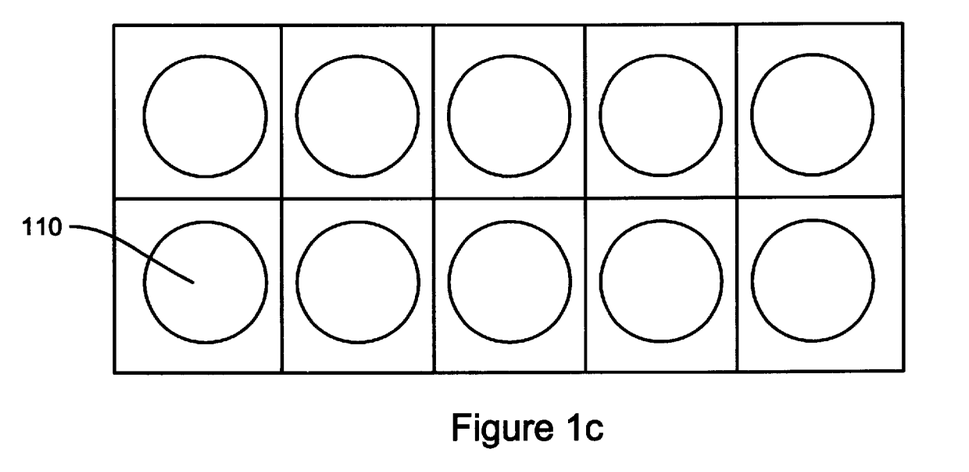
FIG. 1c is top view of the dispenser of FIG. 1a showing dispensing chambers arranged in multiple rows of chambers.

FIGS. 1a, 1b, and 1c show exemplary arrangements of the dispenser having one or more dispensing chambers 110 in accordance with the present invention. The chambers 110 may be singular, as in FIG. 1a, or multiple chambers may be joined as in FIG. 1b or 1c, or in any other desired arrangement. Each chamber 110 is capable of containing items in a small, hermetically sealed area, until such time as use of the contained items is required. The material between the chambers is preferably perforated to allow a user to separate one or more dispensing chambers 110, either before or after expending the contents of those chambers.

Figure 2:
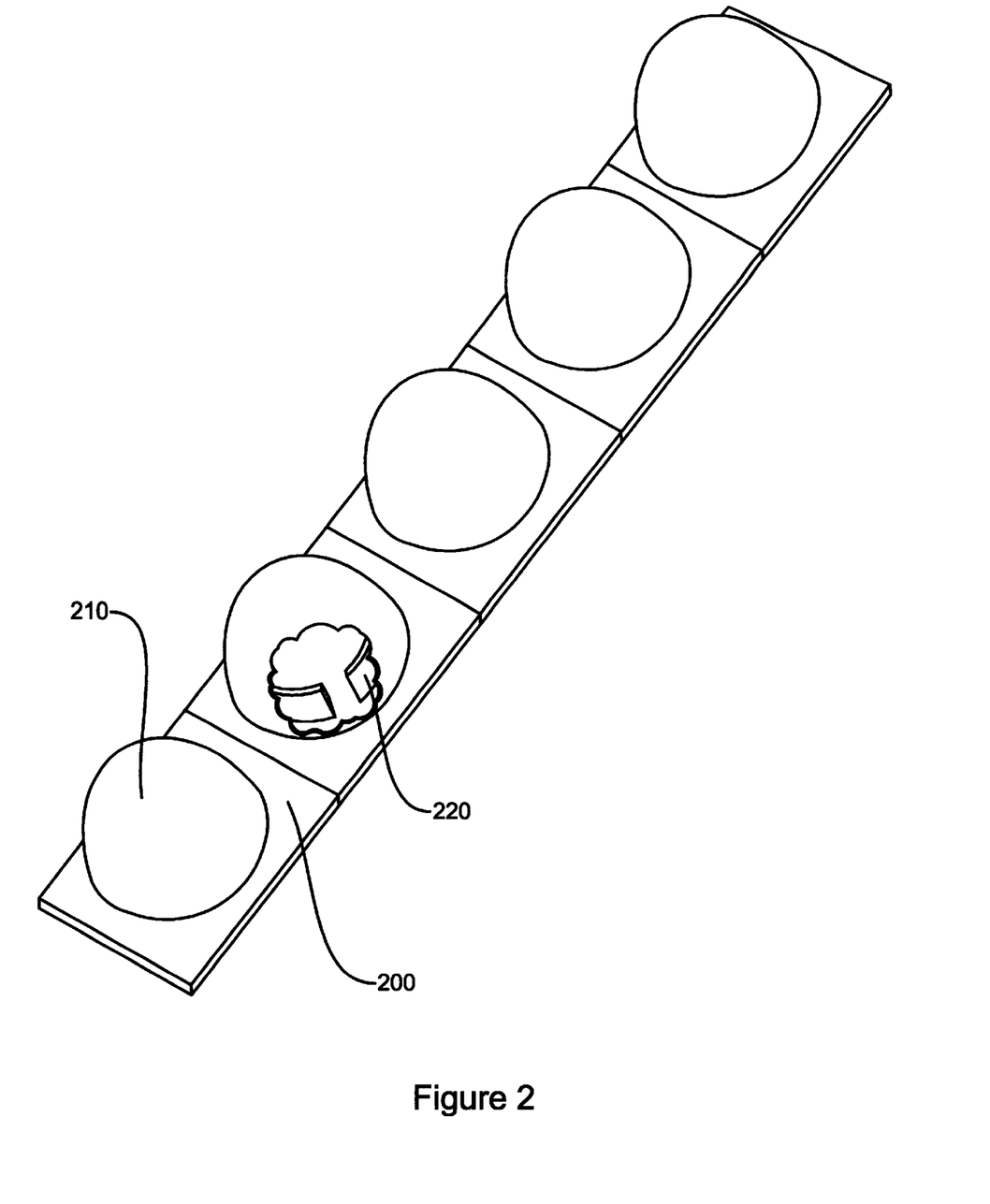
FIG. 2 is a perspective view, partially broken away, of the dispenser of FIG. 1b.

FIG. 2 shows a perspective view of a "strip" of dispensers in accordance with the present invention. Each dispenser is preferably formed of a flexible upper membrane 200 having a depressing dome 210. An internal cutter or punch 220 is disposed within the dome 210.

Figure 3:
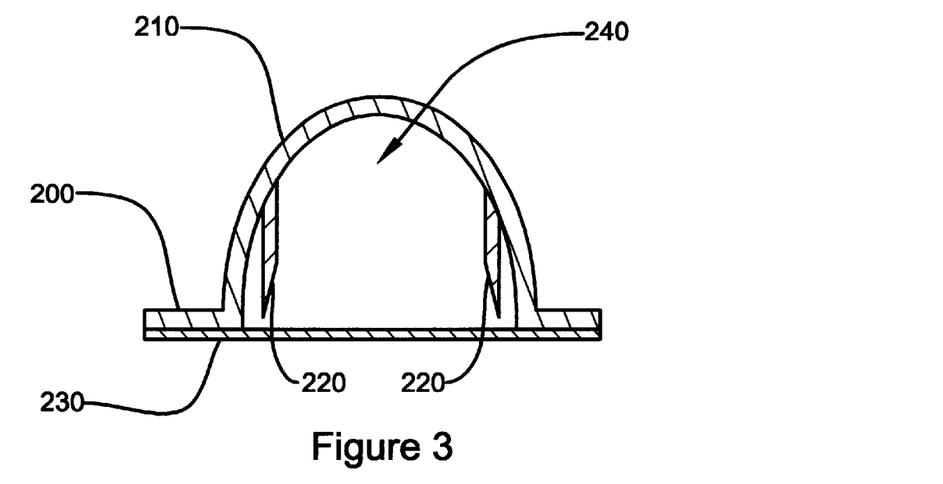

FIG. 3 shows a side view of a preferred embodiment of the present invention showing the flexible upper membrane 200 with the depressing dome 210. This dome 210 is preferably hermetically sealed with a lower membrane 230, to form a dispensing chamber 240, after dispensable items are placed with the dome. The internal cutter 220 is preferably disposed within the dome 210 surrounding one or more dispensable items.

In operation, the internal cutter 220 is forced through the lower membrane 230 as an operator depresses the flexible dome 210. As the dome 210 is depressed, the pressure within the dome increases until the cutters cut through the lower membrane 230. Once the lower membrane 230 is cut, the increased pressure within the dome 210 helps to expel the contents of the dispensing chamber 240.

Components

Figure 4:
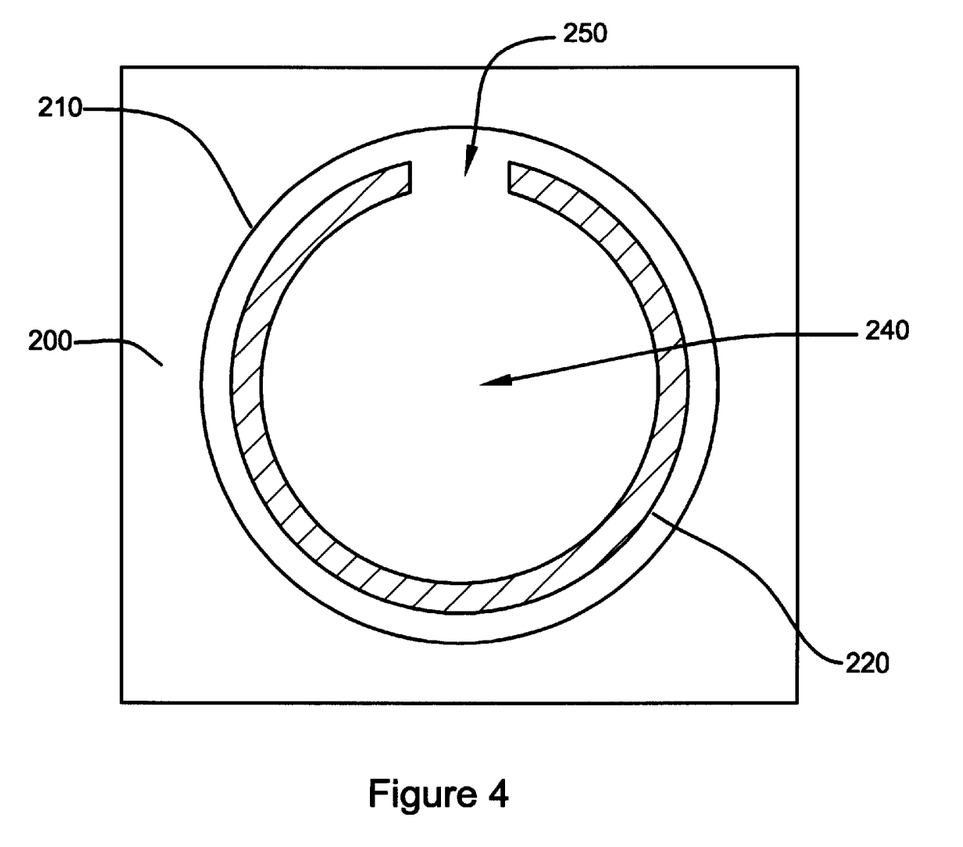

FIG. 4 is a schematic view of the dispenser showing the flexible upper membrane 200, the dome 210, the cutter 220, and the internal chamber 240. The upper membrane 200, dome 210 and internal cutter 220, are preferably of unitary construction, made from a flexible plastic material, preferably in a single injection molding operation. This is advantageous in that the dispenser can be easily and inexpensively manufactured because it is effectively comprised of only two sections, an upper section having the dome 210 with the internal cutter 220 which together form the chamber 240, and a lower section comprising the lower membrane 230 that is used to seal the upper section. However, the dispenser may also be made from other materials of suitable flexibility, and need not be of unitary construction.

The upper membrane 200 is preferably formed of a flexible plastic material. The upper membrane 200 may be made as large or small as desired in order to accommodate the desired number of dispensing chambers 240. For example, as shown in FIGS. 1a through 1c, the upper membrane 200 may consist of a single dispensing chamber 240, or as many dispensing chambers as desired, arranged in multiple rows and/or columns.

The material of the upper membrane 200 between the chambers 240 is preferably segmented and/or perforated such that a user can separate one or more dispensing chambers 240 from the body of the upper membrane, either before or after expending the contents of those chambers. However, in one embodiment, fabrication of the upper membrane without segmentation of the dispensing chambers serves to reduce the production cost.

As shown in FIG. 3, the depressing dome 210 forms an integral part of the upper membrane 200, and is preferably formed at the same time as the upper membrane as one continuous piece. The flexibility of the membrane is preferably such that the dome 210 is stiff enough to protect the contents of the dispensing chamber 240, yet flexible enough to deform downwardly and inwardly when the user applies a downward force to the top of the dome 210.

The cutter 220 is preferably an annular-shaped cutter or punch. As shown in FIG. 4, the cutter 220 preferably has a gap or notch 250 in its circumference. The notch 250 prevents the lower membrane 230 from being completely cut loose from the dispenser during use. Further, the notch 250 is sufficiently narrow that the small portion of the lower membrane 230 that is not cut during operation will not interfere with dispensation or egress of the chamber 240 contents. The cutter 220 creates a hole through the lower membrane 230 sufficient to provide an open path for rapid and complete evacuation of the chamber contents.

Figure 5:
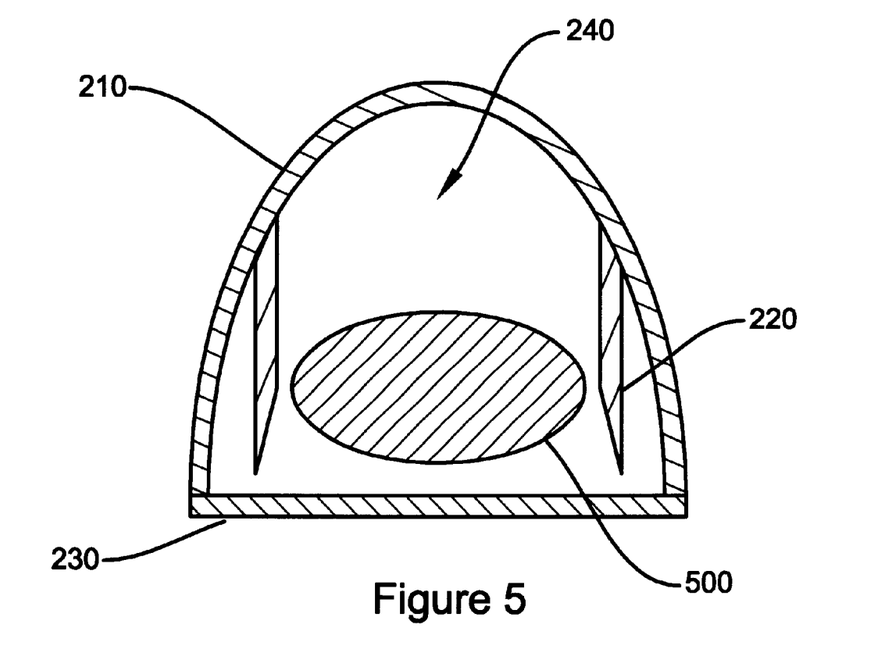
FIG. 5 is cut-away side view of the dispenser of FIG. 1a, shown with a stored item.
Figure 6:
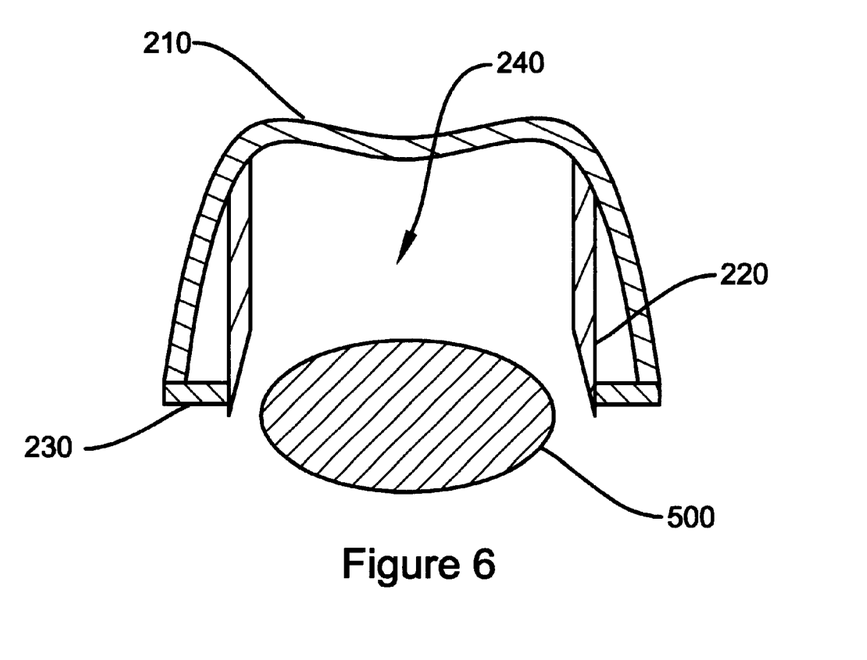
FIG. 6 is cut-away side view of the dispenser of FIG. 1a, shown with the dispenser in use.

The cutter 220 is preferably disposed within the dome 210 and is oriented between and perpendicular to the upper and lower membranes 200 and 230, respectively. The upper end of the cutter 220 is preferably attached to the interior surface of the dome 210, with the bottom end of the cutter floating above the lower membrane 230 prior to use. As shown in FIGS. 5 and 6, the lower end of the cutter 220 is sufficiently sharp to easily and rapidly cut through the lower membrane 230 when the user depresses the dome 210. However, the cutter 220 is preferably not sharp enough to cut through skin, or otherwise cause injury to the user as it protrudes beyond the lower membrane 230 during and after use.

The dispensing chamber 240 is disposed within the depressing dome 210. The sides of the dispensing chamber 240 are formed by the interior of the structure of the annular cutter 220. The top of the chamber 240 is formed by the interior of the depressing dome 210 (which is formed from the upper membrane 200), while the lower membrane 230 forms the bottom of the chamber. Consequently, items stored within the chamber 220 are surrounded by the cutter 220, and covered by the upper and lower membranes 200 and 230.

The lower membrane 230 is preferably formed from a metal foil or plastic material. The lower membrane 230 is preferably of sufficient strength to prevent inadvertent tearing or rupturing of the membrane, even when carried in a relatively hostile environment, such as with metal keys in a users pocket. However, the strength of the lower membrane 230 is such that the cutter 220 is capable of cutting through this membrane by simply depressing the dome 210 using a reasonable amount of force.

The lower membrane 230 is bonded to the base of the upper membrane 200 once the chambers 240 are filled with the desired contents. Bonding of the lower membrane 230 to the upper membrane 200 creates a hermetically sealed storage chamber 240 which protects the stored items until such time as the user depresses the dome 210 to cut the lower membrane and eject the chamber contents.

Operation

FIG. 5 shows an item such as a pill 500 stored within the internal chamber 240 within the internal diameter of the cutter 220. In operation, a user preferably depresses the depressing dome 210 which forces the cutter 220 through the lower membrane 230, thereby opening the lower membrane and allowing the release of the pill 500, or other contents of the chamber 240 to the user.

Unlike with more complicated devices which require manipulation of external cutter devices, or carefully peeling back a membrane or seal, a user having unsteady or shaking hands would typically be able to depress the dome 210 to open the chamber 240 thereby releasing the contents.

Because the lower membrane 230 is cut to allow egress of the chamber 240 contents, the dispenser of the present invention ensures that the contents of the chamber are not forced through the lower membrane as is typical of other "blister pack" type devices. This feature is advantageous in that it may be difficult or impossible to rupture or break a lower membrane without a cutter or punch where the chamber contains a liquid, powder, or other relatively soft item. In addition, use of the cutter 220 prevents damage to relatively soft items, such as nitroglycerin pills, which could not be forced through a membrane or seal without being pulverized.

Further, as shown in FIG. 6, the volume of the chamber 240 decreases as the dome 210 is depressed. Because the dome 210 is flexible, it deforms downwardly and inwardly when pressure is applied to its top surface, thereby decreasing the volume within the chamber 240. Consequently, the internal pressure within the chamber 240 is increased as the volume is decreased prior to cutting the lower membrane 230. The increased pressure preferably assists in expelling or propelling the contents out of the chamber 240 as the cutter 220 cuts the lower membrane 230. This feature is especially useful in ensuring complete and rapid dispensing of powders or liquids from within the chamber 240.

Working Example

Figure 7:
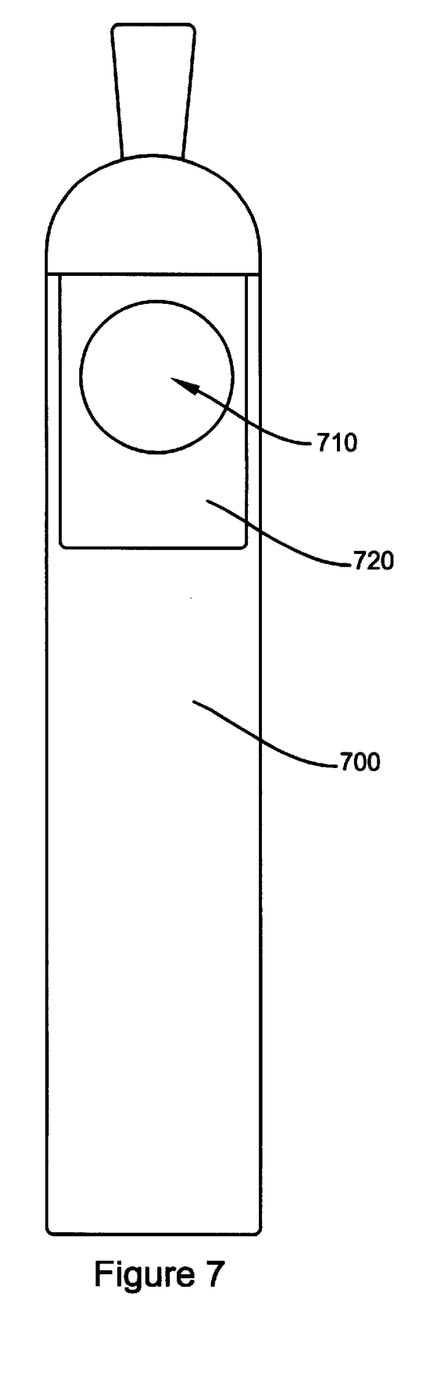
FIG. 7 is a top view of a medical inhaler, which can be used with the dispenser of FIG. 1b.
Figure 8:
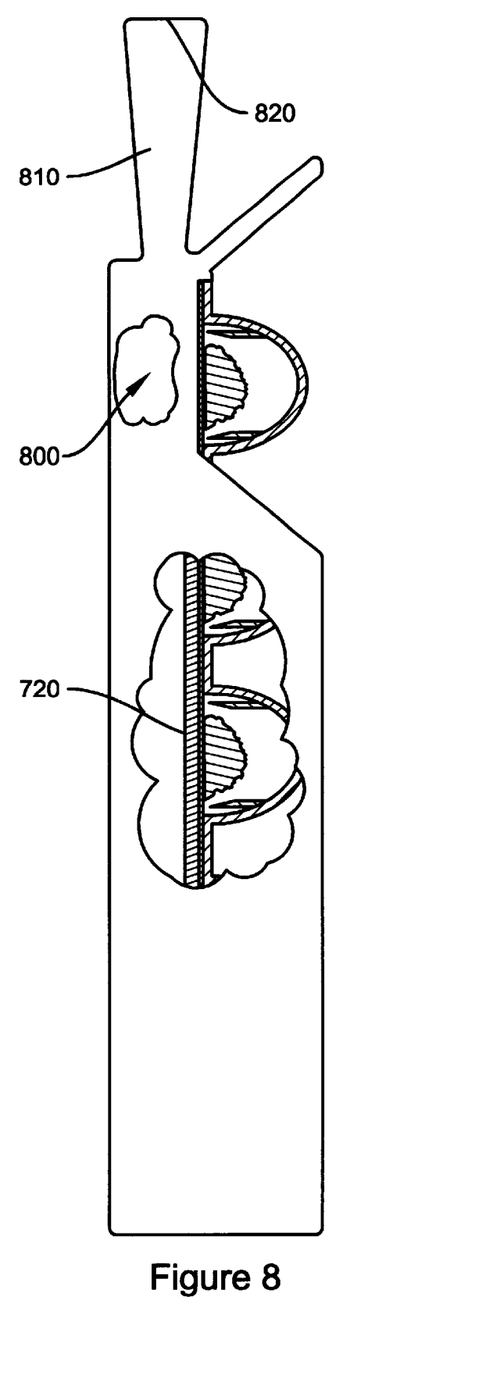
FIG. 8 is a side view of the medical inhaler of FIG. 6, partially broken away, shown in use with the row of dispensers of FIG. 1b.

In one embodiment, the dispenser may be used with a medication carrier/inhaler for powdered medication as shown in FIGS. 7 and 8. The inhaler 700 preferably holds a strip of dispensers, for example, a strip as illustrated in FIG. 1b. The inhaler 700 has a through-hole 710 in a platform 720 that holds the strip of dispensers within the body of the inhaler. As illustrated in FIG. 8, the inhaler is preferably hollow, having a central chamber 800 that is axially divided by the platform 720. The through-hole 710 opens to the central chamber 800 which in turns opens to an annular mouth-piece 810 having an opening 820 that is used by the user to inhale powdered medication from the dispenser.

Figure 9:
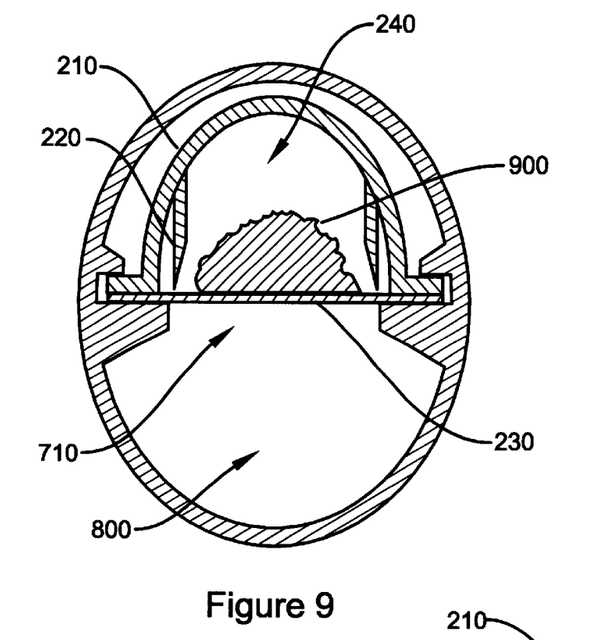
FIG. 9 is a cut-away end view of the medical inhaler of FIG. 6.
Figure 10:
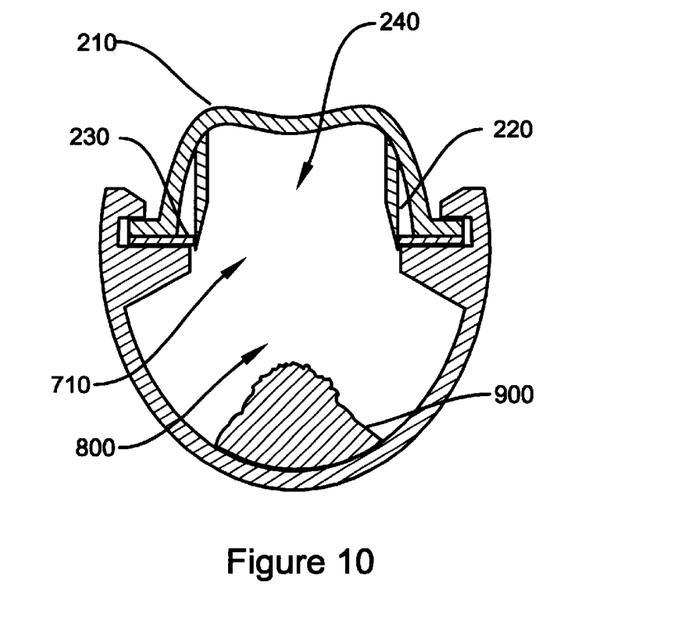
FIG. 10 is a cut-away front view of the medical inhaler of FIG. 6, shown after depressing the dispenser.

As illustrated in FIGS. 9 and 10, when the user requires a dose of powdered medication 900, he or she simply places a dispenser above the through hole 710 and depresses the dome 210 to increase the pressure within the chamber 240 and force the cutter 220 through the lower membrane 230, thereby facilitating the release/expulsion of the chamber contents into the central chamber 800 of the inhaler 700. Further, as discussed in detail previously, the notch in the circumference of the cutter 220 prevents the lower membrane 230 from being completely cut loose from the dispenser during use, while ensuring that the uncut portion of the lower membrane does not interfere with dispensation or egress of the chamber 240 contents. Consequently, the cut portion of the lower membrane 230 can not enter the central chamber 800 where it could be inadvertently inhaled by the user.

Once the chamber 240 contents enter the central chamber 800, the user may immediately inhale the powdered medication 900 via the mouthpiece 810 of FIG. 8. Because the dispenser strip is preferably segmented and/or perforated, as described above, the user can then separate the expended dispenser from the remaining full dispensers. The dispenser/inhaler combination will then be ready for the next use.

The foregoing description of the invention has been presented for the purposes of illustration and description. It is not intended to be exhaustive or to limit the invention to the precise form disclosed. Many modifications and variations are possible in light of the above teaching. For example, the dispenser may be scaled to any desirable size to carry larger or smaller items such as, for example, electronic components or food items. Further, the shape of the dome may be varied without adversely affecting its utility. For example, the dome may be hemispherical, cubical, or any other shape capable of containing a cutter and the dispensable items. It is intended that the scope of the invention be limited not by this detailed description, but rather by the claims appended hereto.

What is claimed is:

1. A dispenser for dispensing one or more sealed items comprising:
   an upper membrane;
   a flexible dome extending from the surface of the upper membrane;
   a frangible lower membrane bonded to the bottom of the upper membrane; and
   an annular cutter extending down from the interior surface of the dome toward the frangible lower membrane.

2. The dispenser of claim 1 further comprising:
   a dispensing chamber defined by the interior circumference of the annular cutter, the dome, and the lower membrane; and
   at least one sealed item held within the dispensing chamber.

3. The dispenser of claim 1 wherein the dome is deformable so that it deforms downwardly when an external downward force is applied to the top of the dome.

4. The dispenser of claim 3 wherein a distal edge of the cutter is sharp so that it cuts through the lower membrane as a result of the downward deformation of the dome.

5. The dispenser of claim 4 wherein the space formed within the dome is initially airtight so that the downward deformation of the dome increases the pressure within the dome prior to the cutter cutting through the lower membrane.

6. The dispenser of claim 5 wherein the increased pressure within the dome assists in expelling the one or more sealed items after the lower membrane is cut.

7. The dispenser of claim 4 wherein the annular cutter has a longitudinal gap such that when the cutter cuts through the lower membrane to release the sealed item, a small section of a resulting cut portion of the membrane remains attached so as to prevent the cut portion from being released with the one or more sealed items.

8. The dispenser of claim 2 wherein the one or more sealed items are powder.

9. The dispenser of claim 2 wherein the one or more sealed items are liquid.

10. The dispenser of claim 2 wherein the one or more sealed items are solid.

11. The dispenser of claim 1 wherein the sealed items are hermetically sealed.

* * * * *